United States Patent [19]

Kettner et al.

[11] Patent Number: 4,952,493
[45] Date of Patent: Aug. 28, 1990

[54] PEPTIDE SUBSTRATES FOR DETECTING VIRUS-SPECIFIED PROTEASE ACTIVITY

[75] Inventors: Charles A. Kettner; Bruce D. Korant, both of Wilmington, Del.

[73] Assignee: E. I. du Pont de Nemours and Company, Wilmington, Del.

[21] Appl. No.: 37,963

[22] Filed: Apr. 13, 1987

Related U.S. Application Data

[62] Division of Ser. No. 06/690,731, Jan. 11, 1985, abandoned.

[51] Int. Cl.$^5$ .......................... C12Q 1/70; C12Q 1/38; C12Q 1/36
[52] U.S. Cl. .......................... 435/5; 435/23; 435/24; 530/300; 530/330; 530/345; 530/802; 530/807; 530/826
[58] Field of Search .............. 435/5, 23, 24, 68, 70; 530/300, 330, 345, 802, 826, 807

[56] References Cited

FOREIGN PATENT DOCUMENTS 8200641 3/1982 PCT Int'l Appl. .

OTHER PUBLICATIONS

Korant, "Inhibition of Viral Protein Cleavage" in *Antiviral Chemotherapy*, Gauri, ed., (Academic Press, New York, 1981).
Korant, "Regulation of Animal Virus Replication by Protein Cleavage", in *Proteases and Biological Control*, (Cold Spring Harbor Laboratory, 1975).
Lozitskii et al., *Usp. Sovrem. Biol.* 93: 352–362 (1982).
Korant et al., *Proc. Natl. Acad. Sci. USA* 76: 2992 (1979).
Korant et al., *Ann. N.Y. Acad. Sci.* 343: 304 (1980).
Korant et al., "Picornaviruses and Togaviruses: Targets for Design of Antivirals", in *Targets for the Design of Antiviral Agents*, DeClercg et al., ed. (Plenum, New York, 1984).

*Primary Examiner*—Jack Spiegel

[57] ABSTRACT

A method for preparing selected peptide substrates for detecting the activity of virus-specified proteases is provided. Specific tetrapeptide substrates are disclosed which are conjugates of protease-cleavable indicator groups and peptide sequences resembling picornavirus protease cleavage recognition sites.

5 Claims, 2 Drawing Sheets

FIG. 2

Picornaviruses

| | |
|---|---|
| Poliovirus (nascent) | leu thr thr tyr/gly phe gly his<br>asp ala met tyr/gly thr asp gly |
| Poliovirus (intermediate) | pro arg leu gln/gly leu pro val*<br>ala leu ala gln/gly leu gly gln*<br>ala leu phe gln/gly pro leu gln*<br>ala met gln gln/gly ile thr asn<br>val ile lys gln/gly asp ser trp<br>ala gly his gln/gly ala tyr thr |
| Poliovirus (maturation) | pro met leu asn/ser pro asn ile |
| FMDV (structural) | pro ser lys gln/gly ile phe pro<br>pro arg thr gln/thr thr ser thr<br>lys gln leu leu/asn phe asp leu |
| FMDV (non-structural) | glu/gly leu ile val |
| FMDV (maturation) | ala leu leu ala/asp lys lys thr |

Alphaviruses

| | | |
|---|---|---|
| Core/E3 (nascent) | ser glu glu trp/ser ala pro leu<br>thr • • •/• • • • | SVF<br>Sindbis |
| 6K/E1 (nascent) | ala pro val ala/cys ile leu ile<br>lys val asp •/tyr gln his ala | SVF<br>Sindbis |
| E3/E2 | arg his arg arg/ser val ser gln<br>• ser lys •/• • ile asp | SVF<br>Sindbis |
| E2/6K | arg ala his ala/ala ser val ala<br>ser • asn •/glu thr phe thr | SVF<br>Sindbis |

PEPTIDE SUBSTRATES FOR DETECTING VIRUS-SPECIFIED PROTEASE ACTIVITY

RELATED APPLICATION

This application is a divisional of our copending application U.S. Ser. No. 690,731, filed Jan. 11, 1985 now abandoned.

BACKGROUND OF THE INVENTION

This invention relates generally to the field of diagnosis of infectious disease, and particularly to compounds and methods for detecting infection by viruses which encode specific proteases.

Proteases are enzymes which cleave proteins at specific peptide bonds. In living systems, highly specific proteases and complementary protease inhibitors mediate or control a broad spectrum of biological functions. For example, proteases cleave precursors to form active proteins in post-translational processing of polypeptides, provide mechanisms for zymogen activation cascade reactions such as blood coagulation, fibrinolysis, and complement reactions of the immune system, and mediate transport of selected proteins across biological membranes.

Proteases encoded by viral genomes play a critical role in replication of many viruses. Viral proteases cleave large precursor polypeptides, produced by infected cells, into smaller protein components, or subunits, which are subsequently assembled to form functional virus structures. Lozitskii et al., *Usp. Sovrem. Biol.* 93:352–362 (1982), discuss the role of proteolysis in replication of avian and mammalian viruses, and have surveyed part of the literature relating to viral protease inhibitors.

Post-translational processing of viral polypeptides by a virus-specified protease occurs in replication of several important families of animal viruses, including the following:

| Virus Family | Representative Genera |
| --- | --- |
| Picornaviruses | poliovirus |
| | rhinovirus |
| | coxsackiesvirus |
| | foot-and-mouth disease virus |
| | hepatitus A virus |
| | cardivirus |
| Togaviruses | rubella virus |
| | yellow fever virus |
| | dengue virus |
| | equine encephalitis virus |
| Retroviruses | various types |
| Adenoviruses | various types |

A role for a virus-specified protease has also been proposed in replication of other virus families, notably myxoviruses, paramyxoviruses, vaccinia viruses, comoviruses, and reoviruses. Korant, "Inhibition of Viral Protein Cleavage", in *Antiviral Chemotherapy*, Gauri, ed., (Academic Press, New York, 1981) and Korant, "Regulation of Animal Virus Replication by Protein Cleavage", in *Proteases and Biological Control*, (Cold Spring Harbor Laboratory, 1975) are reviews of literature relating to virus-specified proteases.

Picornaviruses, which are important pathogens in man and animals, are exemplary of viruses which encode a specific protease involved in viral reproduction.

Picornaviruses are small, non-enveloped, RNA-containing viruses which are important pathogens in man and other mammals. Prototypical of the picornavirus family are polioviruses, which are the causative agents of poliomyelitis, a well-known and devastating disease of the central nervous system. In previous decades, poliovirus epidemics caused paralytic disease in thousands of children and young adults, spurring research which led to effective immunization and near-eradication of the disease in industrialized Western nations. Today, in densely-populated regions where sanitation is primitive, poliovirus remains widespread. Although some children are affected, the majority of the population in such areas have antibodies to the major poliovirus types. In Western countries, however, the virus is much less prevalent. Occasionally, clinically significant cases arise among non-immunized individuals.

Other picornaviruses affecting man include coxsackie viruses, which have been associated with mild intestinal infections; rhinoviruses, which are associated with colds and minor respiratory infections; hepatitis A virus; and cardioviruses, implicated in encephalomyocarditis.

Foot-and-mouth disease viruses (FMDV) are a genus of picornaviruses which afflict cattle and other cloven-hooved animals. Foot-and-mouth disease is extremely contagious, and entire herds containing infected animals are destroyed when an outbreak of the disease is confirmed. The economic consequences of a foot-and-mouth disease epidemic can thus be quite severe. Vaccines have been produced which confer a measure of protection against infection by FMDV, but the disease persists in many areas.

The picornaviruses follow a generally similar pattern of replication. First, infectious virus particles bind noncovalently to specific receptors on the surface of a target cell. Virus particles then penetrate the cell membrane and uncoat a single-stranded viral RNA molecule. This positive-stranded RNA initially serves as an mRNA template for synthesis of viral proteins, including a viral RNA polymerase. The viral RNA polymerase catalyzes synthesis of minus-stranded, or complementary, RNA's, which serve as templates for subsequent production of additional plus strands. As the process of infection proceeds, proportionately more of the newly-synthesized plus strands are incorporated into mature virions.

In addition to a viral RNA polymerase, the viral genome also specifies four major capsid structural proteins, designated $VP_1$, $VP_2$, $VP_3$ and $VP_4$; an RNA capping protein designated $VP_G$; and several non-structural proteins, including a virus-specified protease. The virus-specified protease plays a unique role in picornavirus replication, and provides a target for the diagnostic substrates and methods of the present invention.

Following a virus-induced shutdown of host cell protein synthesis, viral mRNA is translated to viral protein in a continuous passage of host ribosomes along viral mRNA templates. The resulting translation product is a polyprotein containing several domains, each having a different function. This polyprotein is cleaved, prior to dissociation of the ribosome/protein complex, by host cell and virus-specified proteases. Nascent cleavage reactions, which occur essentially instantaneously, are apparently mediated by cellular proteases associated with the host cell translation apparatus. A series of intermediate cleavage reactions, which induce conformational changes and other alterations in tertiary structure eventually culminating in capsid assembly, are then catalyzed by a highly specific, virus-coded protease. Proteolytic cleavages also regulate RNA synthesis by activating and deactivating the viral RNA polymerase.

The existence of a unique, virus-specified protease in cells infected by picornavirus has been demonstrated by several lines of inquiry. First, as detailed below, the virus-specified protease activity is highly site-specific, and does not resemble proteolytic activity associated with normal cellular degradative pathways. Second, this site-specific enzyme activity is not detected in extracts of uninfected cells, but is found in lysates of infected cells in quantities which increase both as the process of infection proceeds, and as the quantity of infecting virus is increased. Third, cell-free protein synthesizing systems, programmed with viral mRNA, produce a characteristic protease activity which also processes capsid polypeptides. Fourth, it has been demonstrated in both infected cells and in cell-free systems that the viral protease is not efficient at cleaving proteins of heterologous viruses or cellular proteins.

As noted above, the virus-specified protease is highly site-specific. In the past several years, the amino acid sequences of cleavage sites recognized by virus-specified proteases have been determined for several picornaviruses. This data has been in part provided by end-group analyses of viral proteins, but additional information has been provided by sequencing viral genomic RNA, or DNA complementary to viral RNA. Comparisons of cleaved sites in picornaviruses have revealed several classes of cleavage recognition sites. The nascent cleavage sites processed essentially instantaneously during translation resemble chymotrypsin cleavage sites; new carboxyl termini are typically donated by aromatic or hydrophobic residues. Intermediate, or subsequently-processed cleavage sites, which are recognized by a virus-specified protease, are quite distinct. In the case of picornaviruses, these sites are characterized by a glutamine-glycine or glutamic acid-X linkage, frequently surrounded by hydrophobic (leucine, isoleucine, or valine) sequences. A high degree of conservation among the cleavage site sequences recognized by virus-specified protease suggests that artificial substrates, designed to mimic the structure of the conserved sequence, can be employed to detect the presence of specific protease activity, and hence, infection of cells by picornavirus.

Togaviruses are a family of RNA-containing viruses, typically arthropod-borne, which include the pathogens of yellow fever, rubella (measles), dengue fever, encephalitis, and certain subclinical conditions. Like picornaviruses, togaviruses employ protein cleavages to form all viral polypeptides, and evidence exists that a specific protease is coded by the togavirus genome. As in the case of picornaviruses, highly conserved peptide regions are observed at cleavage sites of viral precursor polypeptides, suggesting a role for a virus-specified protease.

Retroviruses include a number of genera linked to various sarcomas, leukemias, lymphomas and other carcinomas in avian and mammalian species. Adenoviruses are DNA-containing viruses which induce latent infections in lymphoid tissues, which occasionally erupt into acute episodes of respiratory and ocular infection. Like picornaviruses and togaviruses, retroviruses and adenoviruses appear to encode a specific viral protease.

At least two papers have disclosed use of labelled substrates to detect the presence of picornavirus protease activity in lysates of infected cells. Korant et al., *Proc. Natl. Acad. Sci. U.S.A.* 76:2992 (1979), describe experiments in which [$^{35}$S]methionine-labelled viral precursor proteins were obtained by treatment of poliovirus-infected HeLa cells with iodoacetamide, a protease inhibitor. The labelled proteins were added to extracts of HeLa cells obtained at various stages of virus infection. Radioactive cleavage products were analyzed by sodium dodecyl sulfate (SDS) gel electrophoresis. Extracts derived from cells infected by virus contained a characteristic group of lower molecular weight labelled fragments.

Korant et al., *Ann. N.Y. Acad. Sci.* 343:304 (1980), describe use of acetyl-L-phenylalanyl-L-glycyl-L-alanyl-L-leucyl thiobenzyl ester (Ac-Phe-Gly-Ala-Leu thiobenzyl ester) to detect the presence of picornavirus protease activity. Infected cells were disrupted mechanically, substrate was added to the resulting cytoplasmic fraction, and protease activity monitored spectrophotometrically.

It has now been found that certain synthetic peptides, comprising a characteristic amino acid sequence and an indicator group capable of detection following a protease-catalyzed cleavage event, can be employed to rapidly assay virus-specified protease activity. These compounds, as well as diagnostic processes employing such compounds, are useful in diagnosis of infectious disease caused by viruses which encode a specific protease, for example, picornaviruses.

SUMMARY OF THE INVENTION

The present invention provides a process for preparing a specific peptide substrate for detecting proteases which cleave virus-specified polypeptide precursors to form virus-associated proteins, wherein the proteases to be detected are specified by a virus selected from the group consisting of picornaviruses, togaviruses, retroviruses, adenoviruses, comoviruses, and other viruses which encode a viral protease, comprising:
(a) isolating viral protein, RNA, DNA, mRNA, or DNA complementary to viral RNA;
(b) analyzing the protein, RNA, DNA, mRNA, or cDNA to provide an amino acid sequence of a polypeptide precursor of virus-specified proteins;
(c) locating within the amino acid sequence a cleavage recognition site for the virus-specified protease; and
(d) preparing a specific peptide substrate for detecting the virus-specified protease, wherein the substrate comprises a C-terminal indicator moiety linked by an ester or amide linkage to a peptide sequence of three to five amino acids or amino acid analogues, which substantially corresponds to the amino acid sequence located immediately adjacent to and upstream of the cleavage recognition site of the polypeptide precursor.

The present invention also provides products of the foregoing process. Exemplary products are compounds of the formula:

$$R^1-[A^4A^3A^2A^1]-R^2 \qquad (I)$$

and physiologically acceptable salts thereof, wherein
$A^1$ is an amino acid residue selected from the group consisting of Gln, Glu, and Asn;
$A^2$ is an amino acid residue selected from the group consisting of Ala, Leu, Ile, and Val;
$A^3$ and $A^4$ are, independently, amino acid residues of D- or L-configuration selected from the group consisting of Ala, Asn, Arg, Asp, Cys, Gln, Glu, Gly, His, Ile, Leu, Lys, Met, Phe, Pro, Ser, Thr, Tyr, Val, Trp and analogues thereof;

$R^1$ is hydrogen or an N-terminal protecting group; and $R^2$ is —OH or —X, where X is a moiety capable of forming an amide or ester linkage with a C-terminal carbonyl of amino acid residue $A^1$ to provide conjugated X, and further capable of being independently detected as free X following hydrolytic cleavage of the amide or ester linkage.

The present invention also provides methods of detecting picornavirus-specified protease activity in a sample, comprising use of one or more compounds within the scope of the foregoing formula I.

BRIEF DESCRIPTION OF THE DRAWINGS

FIG. 2 is a diagram illustrating amino acid sequence homology among several known virus-specified protease cleavage recognition sites.

DETAILED DESCRIPTION OF THE INVENTION

Figure 1:
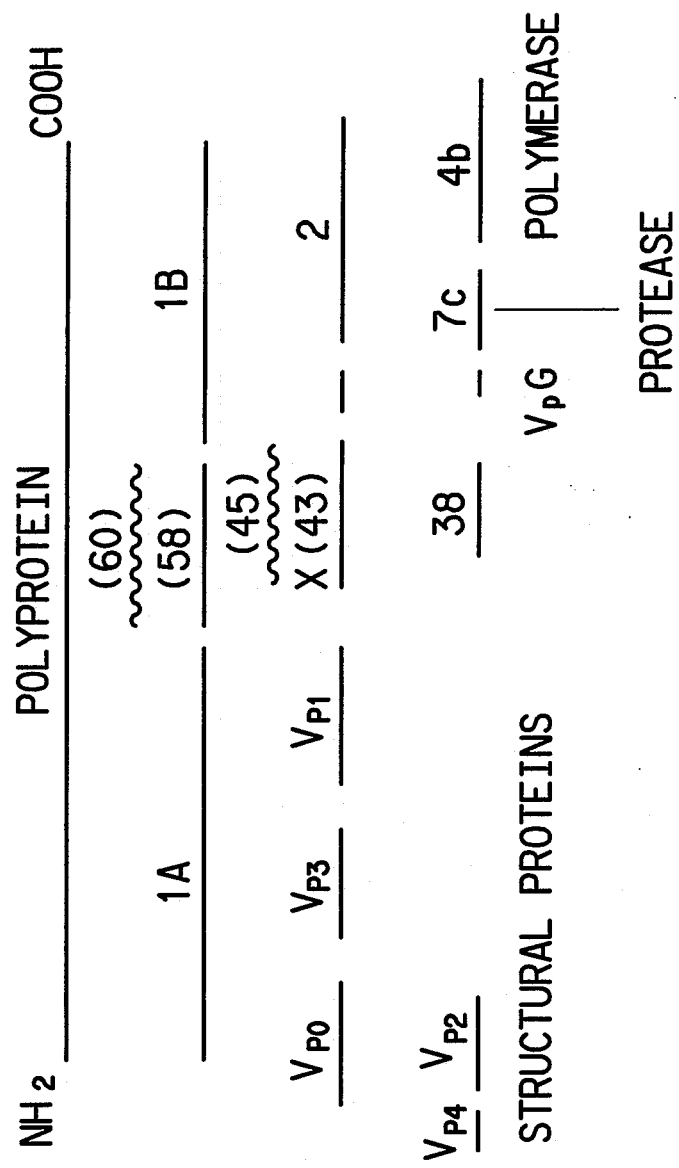
FIG. 1 is a schematic map of the RNA genome of a generalized picornavirus, indicating the relative positions of RNA domains corresponding to particular picornaviral proteins. The direction of translation is from left-to-right.

The method of the present invention provides selected tri-, tetra-, and pentapeptide substrates having C-terminal indicator moieties. These compounds, which are capable of being cleaved by virus-specified proteases, can be employed to detect the presence of viral protease activity in a sample.

Preferably, the sequence of the peptide substrate is exactly homologous to the amino acid sequence immediately adjacent to and upstream of the cleavage recognition sites of the polypeptide precursor. As used herein, "upstream" means in the direction which is the reverse of the direction of translation.

The term "substantially corresponds," as employed throughout the specification in relation to particular peptide sequences, indicates that a subject peptide sequence comprises a like number of amino acid residues as a reference sequence, the identity and sequence of which are exactly homologous or conservatively substituted in relation to the reference sequence. The term "conservatively substituted" as used herein denotes that a given residue has been replaced by a biologically similar residue. Examples of conservative substitution include substitution of one aliphatic residue for another, such as Ile, Val, Leu, or Ala for one another, or substitution of one polar residue for another, such as between Lys and Arg; Glu and Asp; or Gln and Asn. As used above, "residue" means either an amino acid or amino acid analogue.

As previously noted, the amino acid sequences of peptide substrates prepared by the process of the present invention are established by reference to amino acid sequences of cleavage sites recognized by virus-specific proteases. These data can be derived using two general techniques. First, viral proteins can be isolated from purified virus particles or infected cells and dissociated into constituent polypeptides, which are then sequenced from both N- and C-terminals by conventional protein sequence analysis methods (e.g., Edman degradation). This method provides sequence data immediately adjacent to known cleavage sites. Second, RNA genomes (or a cDNA transcript thereof) of certain viruses can be sequenced to provide a primary sequence of nucleotides, from which viral protein sequences are derived using the open reading frame of translation. Cleavage sites are then determined by comparison of the derived amino acid sequences with those of known proteins of homologous or related viruses.

Methods of obtaining and purifying viral proteins or nucleic acids, and of sequencing viral nucleic acids, are well-known, and will not be detailed herein. The following are useful general references relating to suitable methods and are hereby incorporated by reference.

Maxam, A. M., and Gilbert, W., *Proc. Natl. Acad. Sci U.S.A.* 74:560–564 (1977).

Sanger, F., Nickler, S., and Carlson, A. R., *Proc. Natl. Acad. Sci. U.S.A.* 74:5463–5467 (1977).

Peattie, D. A., *Proc. Natl. Acad. Sci. U.S.A.* 76:1760–1764 (1979).

Simoncsits, A., Brownlee, G. G., Brown, R. S., Rubin, J. R., and Guilly, H., *Nature* 269:833–836 (1977).

The references set forth below describe sequencing experiments involving genomes or proteins of particular viruses:

1. Carroll, A. B., Rowlands, D. J., and Clarke, B. E., *Nucleic Acids Res.* 12:2461 (1984); (foot-and-mouth disease virus).

2. Herbert, E., and Muhler, M., *Cell* 30:1 (1982); (alphavirus).

3. Klenk, H. D., Garten, H. D., Keil, W., Niemann, H., Scwarz, R. T., and Rott, R., "Processing of the Influenza Virus Hemagglutinin," in G. Koch and D. Ricter, eds., *Biosynthesis, Modification, and Processing of Cellular and Viral Polyproteins* (Academic Press, New York, 1980).

4. Korant, B., Chow, N., Lively, M., and Powers, J., *Proc. Natl. Acad. Sci. U.S.A.* 76:2992 (1979); (poliovirus).

5. Korant, B., *J. Virol.* 10:751 (1972); (poliovirus).

6. Lee, T. H., Coligan, J. E., Homma, T., McLane, M. F., Tachibana, N., and Essex, M., *Proc. Natl. Acad. Sci. U.S.A.* 81:3856 (1984); (Human T-cell leukemia virus).

7. Oroszlan, S., Henderson, L. E., Copeland, T. D., Schultz, A. M., and Rabin, E. M., "Processing and Structure of Murine Leukemia Virus gag and env Gene Encoded Polyproteins," in G. Koch and D. Richter, eds., *Biosynthesis, Modification, and Processing of Cellular and Viral Polyproteins* (Academic Press, Inc., New York, 1980).

8. Palmenberg, A. C., Kirby, E. M., Janda, M. R., Drake, N. L., Duke, G. M., Potratz, K. F., and Collett, M. S., *Nucleic Acids Res.* 12:2969 (1984); (encephalomyocarditis virus)

9. Seiki, M., Seisuke, H., Hirayama, Y., and Yoshida, M., *Proc. Natl. Acad. Sci. U.S.A.* 80:368 (1983); (Human T-cell leukemia virus).

10. Stanway, G., Et al., *Nucleic Acids Res.* 11:3629 (1983); (poliovirus).

11. Strauss, E. G., Rice, C. M., and Strauss, J. H., *Virology* 133:92 (1984); (Sindbis virus).

Specific exemplary compounds of the present invention are selected tetrapeptides, corresponding to sequences found at picornavirus protease cleavage sites, which comprise a C-terminal reporter or indicator moiety. This indicator, or label, is capable of independent detection following cleavage from the remainder of the peptide molecule. Such labelled peptides are designed to mimic cleavage sites recognized by picornavirus-specified proteases, thereby providing an artificial substrate for measuring picornavirus protease specific activity. The presence of such activity is diagnostic of picornavirus infection.

As used throughout the specification, the following abbreviations for amino acid residues or amino acids apply:

| Amino Acid | One-Letter Abbreviation | Three-Letter Abbreviation |
|---|---|---|
| L-alanine | A | Ala |
| L-argine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |
| L-tryptophan | W | Trp |
| L-tyrosine | Y | Tyr |
| L-valine | V | Val |

Where prefixed by "D-", the foregoing abbreviations indicate an amino acid of D-configuration.

As used throughout the specification, "N-terminal protecting group" means an arylcarbonyl, alkylcarbonyl, alkoxycarbonyl, aryloxycarbonyl, aralkoxycarbonyl, arylsulfonyl, alkylsulfonyl, or arylsulfonyl peptide protecting group, or other equivalents known to those skilled in the art of peptide synthesis. Gross and Meienhofer, eds., The Peptides, Vol. 3, (Academic Press, New York, 1981) pp. 3-81, the disclosure of which is hereby incorporated by reference, describe numerous suitable amine protecting groups. As used herein, either individually or as part of a larger group, "alkyl" means a linear, cyclic, or branched-chain aliphatic moiety of 1 to 10 carbon atoms; "substituted alkyl" means an alkyl group having a substituent containing a heteroatom or heteroatoms such as N, O or S; "aryl" means an aromatic moiety, e.g., phenyl, of 6 to 18 carbon atoms, unsubstituted or substituted with one or more alkyl, substituted alkyl, nitro, alkoxy, or halo groups; and "alkaryl" means an aryl moiety of 7 to 19 carbons having an aliphatic substituent, and, optionally, other substituents such as one or more alkyl, substituted alkyl, alkoxy or amino groups. "Aralkyl" means a linear or branched-chain aliphatic moiety of 6 to 18 carbon atoms comprising an aryl group or groups.

Examples of suitable values for N-terminal protecting group $R^1$ include formyl, acetyl, trifluoroacetyl, benzyloxycarbonyl (carbobenzoxy), substituted benzyloxycarbonyl, tert-butyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenyl, dansyl, p-methoxybenzenesulfonyl, p-toluenesulfonyl, methanesulfonyl and phenylthio.

Certain values for N-terminal protecting group $R^1$ are abbreviated as follows throughout the specification:

| Z | Carbobenzoxy |
|---|---|
| Boc | t-Butyloxycarbonyl |
| Ac | Acetyl |
| Et | Ethyl |
| Suc | Succinyl |
| MeOSuc | Methoxysuccinyl |
| DNS | Dansyl |
| DNP | 2,4-Dinitrophenyl |

Compounds within the invention having side-chain amino groups, for example, where $A^3$ or $A^4$ are Lys or Arg, can optionally comprise suitable N-terminal protecting groups attached to the side chains. Similarly, amino acid residues having acidic or hydroxy side chains, for example, $A^1$, $A^3$, or $A^4$, can be protected in the form of methyl, benzyl or other suitable esters or ethers.

As noted previously, $A^3$ and $A^4$ can be amino acids of D-configuration or analogues of amino acids. As used throughout the specification, "analogue" means a residue of the formula

which is not a naturally-occurring amino acid. $R^3$ in the foregoing formula II can be an alkyl, substituted alkyl, aryl, aralkyl, or alkaryl group, optionally terminating in a hydroxy, amino, phosphate, or thio group. Examples of such analogues include hydroxyproline, t-carboxyglutamate, O-phosphoserine, carnitine, cysteic acid, phenylglycine, α-aminoisobutyric acid and α-aminocaproic acid.

Acceptable salts of compounds of formula I include acid addition salts of free base, if present, wherein the acid can be organic or inorganic, e.g., hydrochloric, phosphoric, maleic, acetic, citric, succinic, etc. Alternatively, salts of free peptidic acids, including sodium, potassium, and ammonium salts, are included within the scope of the present invention.

As noted above, substituent $R^2$ in the foregoing formula I can be —OH or X, where X is a moiety capable of forming an amide or ester linkage with a C-terminal carbonyl of amino acid residue $A^1$ to provide a conjugate of X and peptide. Moiety X is also capable of being independently detected as free, or non-conjugated X, following cleavage of the amide or ester linkage by a virus-specified protease. Thus, for example, moiety X will comprise an amino group or hydroxyl group at a position convenient for forming a peptide bond to amino acid residue $A^1$, as illustrated by the following formula III:

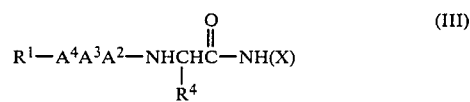

In the case of tetrapeptide substrates for detecting picornavirus protease activity, residue $A^1$ is selected from the group consisting of Gln, Glu, or Asn. Accordingly, the value of substituent $R^4$ in the foregoing formula is selected from the group consisting of —CH$_2$CH$_2$COOH, —CH$_2$CONH$_2$, and —CH$_2$CH$_2$CONH$_2$, as well as variants of the foregoing radicals comprising suitable protecting groups as previously described.

The precise identity and nature of indicator moiety X is not critical to the present invention, so long as the foregoing conditions are satisfied. It is presently contemplated that X can be a chromogenic, fluorogenic, chemiluminescent, radioactive, antigenic or haptenic group detectable by one of the many techniques known in the art for detecting particular analytes or ligands in solution. Further details regarding suitable values for X are provided below.

Where X is a chromogenic group, free X in solution will be detectable spectrophotometrically following cleavage from the remainder of the peptide. Examples of suitable chromogenic groups include nitroanilino, nitrophenyloxy, 2,4-dinitrophenyloxy, nitrophenylamino, naphthylamino, nitronaphthylamino, methoxynapthylamino, quinolylamino, nitroquinolylamino, and 4-trifluoromethylcoumaryl-7-amino. A preferred chromogenic group is naphthylamino, especially β-naphthylamino, hereinafter abbreviated as "NA".

Where X is a fluorogenic group, free X will be detectable in solution by exciting at one wavelength and detecting at another, following cleavage of the indicator group from the remainder of the peptide. Exemplary suitable fluorogenic groups include 4-methylcoumaryl-7-amino, hereinafter abbreviated as "AMC", 4-trifluoromethylcoumaryl-7-amino, naphthylamino, 7-oxycoumaryl, 4-methylumbelliferone, and 5-amino-isophthalic acid diethyl ester. Of the foregoing, AMC is preferred.

X can also be a chemiluminescent indicator group, for example, aminoisoluminol.

Where X is a group comprising a radioactive atom or atoms, for example, [$^{14}$C], [$^{35}$S], or [$^{3}$H], a system or procedure for partitioning free X from conjugated X must be provided. For example, such partitioning can result from separation of organic and aqueous solutions. Examples of indicator groups which can be partitioned into an organic phase include anilino, benzylamino, or lower alkoxy groups containing one or more [$^{14}$C] or [$^{3}$H] groups. Following incubation of a radioactively labelled substrate with a sample suspected to contain specific protease activity, an organic solvent, e.g., toluene, can be added to assay mixtures. Due to the higher solubility of free X in organic solvents, a relatively high proportion of free X will be extracted into the organic solvent, which can be drawn off, added to a scintillation vial containing a liquid scintillation cocktail, and counted by known techniques.

Alternatively, free radioactive indicator groups can be partitioned from conjugated groups by means of a ligand binding system which immobilizes free radioactive indicator groups on a solid substrate or immobilized substrate can be used and the liberated indicator monitored.

Where X is an antigenic or haptenic group independently detectable by specific antibody, antibody reagents, especially monoclonal antibodies, are required which recognize free X yet fail to recognize, or show reduced binding affinity, for conjugated X. An example of a suitable haptenic indicator group is ortho-nitrophenol. Any of several known immunological techniques can then be employed to detect protease activity. Examples of such techniques include radioimmunoassay or enzyme immunoassay, particle enhanced turbidimetric immunoassay, and affinity column mediated immunoassay.

In a conventional radioimmunoassay or enzyme immunoassay, added enzyme- or radioisotope-labelled hapten, in addition to hapten (free X) produced by protease-catalyzed hydrolysis of labelled substrate, compete for a limited number of binding sites on hapten-specific antibody. The amount of activity bound by antibody, which can be quantified by known techniques, is inversely related to the amount of hapten, or free X, generated by specific protease activity.

In a particle-enhanced turbidimetric immunoassay, particles are coated with a hapten or other molecular species which is also bound to substrates as indicator group X. The resulting X-coated particles are then incubated with antibody specific for X, in addition to a sample which has previously been incubated with an X-labelled peptide substrate. Presence of free X liberated by specific protease activity inhibits formation of turbidity which would otherwise result from the action of X-specific antibody upon the coated particles.

In an affinity column-mediated immunoassay, an enzyme-labelled antibody specific for an indicator group X is incubated with a sample containing, or suspected to contain, specific protease activity, and with X-labelled peptide substrate. Following incubation, the resulting mixture is applied to a column containing a solid substrate also bound to haptenic or antigenic group X. Enzyme-labelled antibody which bound X during incubation with sample will pass through the column and be collected in the column effluent. Free antibody will be bound by the column. The amount of enzyme activity in the column effluent can then be assayed. The resulting quantity is related to the amount of free X liberated during incubation with sample.

The characteristic peptide sequences which identify exemplary compounds within the scope of the present invention were established by reference to known amino acid sequences of cleavage sites recognized by virus-specific proteases. This data was derived using two general techniques. First, viral proteins were isolated from purified virus particles or infected cells and dissociated into constituent polypeptides, which were then sequenced from both N- and C-terminals by conventional protein sequence analysis methods (e.g., Edman degradation). This method provided sequence data immediately adjacent to known cleavage sites. Second, RNA genomes (or a cDNA transcript thereof) of certain viruses were sequenced to provide a primary sequence of nucleotides, from which viral protein sequences were derived using the open reading frame of translation. Cleavage sites were then determined by comparison of the derived amino acid sequences with those of known proteins of homologous or related viruses.

The homology between cleavage sites of certain viral proteins is illustrated by FIG. 2. In FIG. 2, 22 known cleavage sites are listed, in addition to sequence information for proteins of poliovirus type 1, foot-and-mouth disease virus, semliki forest virus and sindbis virus. Cleavage sites recognized by virus-specified proteases are indicated by a slashed line, and exact homology is indicated by filled circles. The information set forth in FIG. 2 suggests that cleavage sites for picornaviruses are frequently marked by the presence of glutamine-glycine or glutamic acid-glycine sequences, often surrounded by hydrophobic residues such as alanine, valine, isoleucine, or leucine. Other cleavage sites which have thus far been been characterized contain an asparagine residue. The identities of residues more distant from the cleavage sit than residue $A^2$, i.e., residues $A^3$ and $A^4$, are not presently thought to significantly affect the specificity of the resulting synthetic substrate.

There is a greater diversity at cleavage sites of togavirus structural proteins. In the case of alphaviruses, a subset of the togavirus family, alanine residues tend to be present. Moderate to high conservation of individual sites has been observed in comparisons of Semliki Forest virus and Sindbis virus, although different sites show substantial chemical differences, suggesting participation by several proteases. All cleavages can be considered chymotryptic-like, except for a dibasic arg-arg/ser or lys-arg/ser site cleaved between envelope proteins 2 and 3.

A contemplated genus of compounds within the scope of the present invention includes compounds of formula I, above, where $R^1$ is Boc, Z, Suc, or MeOSuc; $R^2$ is —OH or a chromogenic, fluorogenic, chemiluminescent, radioactive, antigenic, or haptenic indicator group; and $A^1$, $A^2$, $A^3$ and $A^4$ are as defined above. Contemplated classes of compounds within the genus defined above include a first class wherein $A^1$ is Gln; a second class wherein $A^1$ is Glu; and a third class wherein $A^1$ is Asn. Within each of the foregoing three classes, subclasses are contemplated wherein each of the limitations of the class apply and $A^3$ and $A^4$ are selected from the group consisting of Ala, Arg, Asn, Asp, Cys, Gln, Glu, Gly, His, Ile, Leu, Lys, Met, Phe, Pro, Ser, Thr, Trp, Tyr, and Val. Additional subclasses are contemplated wherein $A^3$ and $A^4$ are further selected from Ala, Gly, Ile, Leu, Phe, Ser, Tyr, and Val.

Exemplary compounds within the scope of the present invention include the following, wherein $R^1$ in each of the following formulas is Boc, Z, Suc, or MeOSuc; and $R^2$ in each of the following formulas is a chromogenic, fluorogenic, chemiluminescent, radioactive, antigenic, or haptenic indicator group:

| | | |
|---|---|---|
| $R^1$-FGLQ-$R^2$ | $R^1$-PMLQ-$R^2$ | $R^1$-AKVQ-$R^2$ |
| $R^1$-FALQ-$R^2$ | $R^1$-PTLQ-$R^2$ | $R^1$-VVLQ-$R^2$ |
| $R^1$-FLLQ-$R^2$ | $R^1$-PRLQ-$R^2$ | $R^1$-VVVQ-$R^2$ |
| $R^1$-FILQ-$R^2$ | $R^1$-AKLQ-$R^2$ | $R^1$-LDIQ-$R^2$ |
| $R^1$-FVLQ-$R^2$ | $R^1$-AIAQ-$R^2$ | $R^1$-TQLQ-$R^2$ |
| $R^1$-FGAQ-$R^2$ | $R^1$-AMLQ-$R^2$ | $R^1$-TDVQ-$R^2$ |
| $R^1$-FGIQ-$R^2$ | $R^1$-AELQ-$R^2$ | $R^1$-RHLN-$R^2$ |
| $R^1$-FGVQ-$R^2$ | $R^1$-VILQ-$R^2$ | $R^1$-RSLN-$R^2$ |
| $R^1$-GGLQ-$R^2$ | $R^1$-ALLQ-$R^2$ | $R^1$-ALLE-$R^2$ |
| $R^1$-AALQ-$R^2$ | $R^1$-AILQ-$R^2$ | $R^1$-IHLE-$R^2$ |
| $R^1$-LALQ-$R^2$ | $R^1$-AGLQ-$R^2$ | $R^1$-FGLE-$R^2$ |
| $R^1$-IALQ-$R^2$ | $R^1$-AQLQ-$R^2$ | $R^1$-CTLE-$R^2$ |
| $R^1$-VALQ-$R^2$ | $R^1$-EQLQ-$R^2$ | $R^1$-GGLE-$R^2$ |

Compounds specified by the present invention are generally prepared as follows.

First, N-protected peptides or amino acids are reacted with about one equivalent of N-methylmorpholine and one equivalent of isobutyl chloroformate at about −20° C., generating a mixed peptide-isobutyric acid anhydride. This standard technique is described by Anderson et al., J. Am. Chem. Soc. 89:5012 (1967). Second, the resulting mixed anhydride is treated with about one equivalent of a label compound containing an amino group in N,N-dimethylformamide (DMF) or other suitable inert, aprotic solvent, generating a labelled N-protected peptide or amino acid.

Larger peptides can be assembled by repetitively coupling a deprotected labelled peptide to mixed anhydrides of other N-protected peptides or amino acids generated according to the foregoing procedure. Deprotection of N-terminal amino groups can be accomplished by treatment with trifluoroacetic acid, anhydrous HF, anhydrous HCl, or by other methods known to those skilled in the art.

In use, the peptide substrates of the present invention are incubated with a sample suspected to contain picornavirus protease activity. The incubation is allowed to proceed for a time sufficient to permit protease-catalyzed hydrolysis of substrate. Following incubation, the presence of cleaved indicator groups is detected by methods suitable for the indicator employed. In other cases, liberation of the indicator group can be monitored continuously. Samples can be physiological fluids drawn from humans or animals, for example, serum, plasma, lymph, peritoneal fluid, pleural fluid, saliva, spinal fluid, nasal secretions, or vaginal or cervical secretions. Alternatively, samples can be prepared by growing cells derived from human or animal patients suspected of harboring picornaviral infections. These cells can be grown in tissue culture, and culture supernatants or lysates of cultured cells can be assayed for protease activity using the substrates of the present invention.

Generally applicable procedures suitable for preparing compounds within the scope of the present invention are described in the paragraphs preceding the Examples, below. In the synthetic procedures and Examples, all parts and percentages are by weight, and all degrees are Celsius, unless otherwise noted.

GENERAL SYNTHETIC PROCEDURES

1. Mixed Anhydride Coupling Procedure (MA)

Approximately 1–2 g of an N-protected amino acid or peptide are dissolved in 20 mL of tetrahydrofuran (THF), and the resulting solution is cooled to −20°. N-methylmorpholine (1 eq) and isobutyl chloroformate (1 eq) are added and after 5 minutes, an additional 10 mL of cold THF and one equivalent of triethylamine are added. The resulting mixture is immediately added to an equivalent of an amine hydrochloride or trifluoroacetate dissolved in 5 mL of DMF. The ensuing reaction is allowed to stir 1 hour at −20° and then 2 hours at about 23°. The resulting mixture is filtered and the filtrate thereby obtained is then concentrated to approximately 5 mL by evaporation. The resulting concentrate or redidue is dissolved in ethyl acetate, and then washed sequentially with 0.2N hydrochloric acid, 5% sodium bicarbonate solution, and saturated aqueous sodium chloride. The resulting organic solution is then dried briefly over sodium sulfate, filtered, and finally evaporated to leave a crude peptide product.

2. N-Hydroxysuccinimide (OSu) Coupling Procedure

N-hdyroxysuccinimide esters of N-protected amino acids and peptides can be prepared by procedures substantially similar to those described by Anderson et al., J. Am. Chem. Soc. 86: 1839 (1964). An OSu ester is dissolved in a minimal volume of dioxane, and the resulting solution is added to an equal volume of an aqueous solution consisting of 1.5 eq of triethylamine and either an amino acid (1.5 eq) or a peptide (1.1 eq), forming a reaction mixture. After about 5 minutes, if a complete solution is not obtained, a small test sample of the reaction mixture can be diluted with water and another sample diluted with dioxane. On the basis of the results obtained, the reaction mixture is then diluted with the appropriate solvent (either water or dioxane) until a complete solution is obtained. After the reaction has proceeded to completion, the reaction mixture is acidified with hydrochloric acid and the resulting product extracted into ethyl acetate. The resulting extract is then washed with 0.2N hydrochloric acid followed by 0.2N hydrochloric acid in saturated sodium chloride. The washed extract is then dried over sodium sulfate, filtered, and finally evaporated to dryness to leave a crude peptide.

3. Other Coupling Procedures

Dansyl, 2,4-dinitrophenyl, and methoxysuccinyl derivatives of peptides are prepared by reacting a selected chloride, fluoride, or N-hydroxysuccinimide ester with an appropriate peptide. Acetyl and succinyl derivatives can be prepared from corresponding anhydrides. A peptide hydrochloride or trifluoroacetate salt is dissolved in 50% aqueous dioxane at a level of 0.25 mmol/mL and the resulting solution is cooled to 0°. A selected coupling agent (1.0–1.2 eq) is dissolved in dioxane and added along with 2 eq of sodium bicarbonate. The resulting reaction is monitored by following the disappearance of ninhydrin positive material.

4. Saponification of Methyl Esters

An N-protected methyl ester is dissolved in dioxane (1 mL/mmole), and an equal volume of 1.00N sodium hydroxide is added over a period of 30 minutes. Disappearance of starting material is monitored by thin-layer chromatography. After the resulting reaction has proceeded to completion, an equivalent of 1.00N hydrochloric acid is added, and the solution is diluted to 100 mL with water. The product is then extracted into ethyl acetate, and the resulting extract washed with 0.2N hydrochloric acid followed by 0.2N hydrochloric acid in saturated sodium chloride. Solvent is then removed by evaporation to leave a crude carboxylic acid.

5. Hydrolysis of the Boc Group

Boc protecting groups are removed from peptides by dissolving a selected peptide in trifluoroacetic acid and stirring the resulting solution for 5 minutes at about 23°. Cold ether is then added. If a precipitate is obtained upon addition of ether, it is triturated with ether and isolated. If no precipitate is obtained, the ether is evaporated and toluene added to co-evaporate residual trifluoroacetic acid, yielding the deprotected peptide as a trifluoroacetic acid salt.

Alternatively, a Boc-protected peptide can be dissolved in ethanolic hydrochloric acid (2.0–3.5N) and the resulting solution stirred at about 23° for about 30 minutes, followed by evaporation of solvent. In all cases, peptide hydrochloride or trifluoroacetate salts are dried overnight under vacuum in the presence of solid potassium hydroxide and phosphorus pentoxide.

6. Hydroylsis of t-butyl Esters (Bu)

t-Butyl peptide esters are dissolved in trifluoroacetic acid, and the resulting solution is stirred for 1 hour at about 23° C. Solvent is then evaporated, and the resulting residue is redissolved in toluene. Following a second toluene evaporation step, the remaining residue is dried in vacuo over solid potassium hydroxide. Crude product is crystallized from an appropriate solvent, e.g., toluene or ethyl acetate.

7. Thin-Layer Chromatography (TLC) Procedures

TLCs are run on 5×10 cm silica gel plates, using a fluorescent indictor. Spots are visualized by conventional techniques, using either UV light or an iodine jar. Peptides with free amino groups protected by Boc groups are exposed to HCl vapors, and then stained with ninhydrin. The following solvent systems are useful for chromatography:
methanol:chloroform (1:9)
butanol:acetic acid:water (4:1:1)
ethyl acetate:hexane (8:2)

EXAMPLE 1

Preparatin of Suc-Phe-Gly-Leu-Gln-AMC

Boc-Gln-AMC was prepared by coupling anhydrous Boc-Gln-OH (7.03 g, 28.5 mmol) to 7-amino-4-methylcoumarin (AMC) by the mixed anhydride coupling procedure outlined above. First, a solution of a mixed anhydride of Boc-Gln-OH was prepared by reacting Boc-Gln-OH with an equivalent of N-methylmorpholine and an equivalent of isobutyl chloroformate, and the resulting solution was added to AMC (5.00 g, 28.5 mmol) dissolved in 30 mL DMF. After the resulting reaction was complete, the reaction mixture was filtered and the filtrate concentrated. Product (5 g) was separated from the filtrate and dissolved in 75 mL hot methanol. This solution was then concentrated to about 30 mL and cooled. Solid AMC was separated from the solution by filtration, and the remaining filtrate was further concentrated to a volume of about 5 mL. This concentrated solution was then diluted with 30 mL chloroform, and the resulting solution applied to a 4 cm column containing about 30 g silica gel. Residual AMC was eluted from the column with additional chloroform, and product Boc-Gln-AMC (0.97 g) was then recovered from the column by elution with 2% methanol in chloroform. Recrystallization of product from methanol provided 0.46 g of purified Boc-Gln-AMC, mp 260.5–207°. TLC with methanol:chloroform (1:9) indicated a single spot, Rf 0.28.

Anal. Calcd. for $C_{20}H_{25}N_3O_6$: C, 59.53; H, 6.26; N, 10.4. Found: C, 59.70; H, 6.17; N, 10.56.

Boc-Gln-AMC was deblocked by treatment with trifluoroacetic acid at about 23° for 5 min. Excess trifluoroacetic acid was evaporated at reduced pressure and the resulting residue, H-Gln-AMC trifluoroacetate, was dried in vacuo over solid potassium hydroxide. The resulting product was then washed with ether and redried over solid potassium hydroxide.

Boc-Phe-Gly-Leu-Gln-AMC was prepared by coupling Boc-Phe-Gly-Leu-OH (0.39 g, 0.90 mmol) to H-Gln-AMC trifluoroacetate (0.41 g, 0.99 mmol) by a mixed anhydride coupling procedure to yield 0.49 g crude product. Product was recrystallized from ethyl acetate to provide 0.27 g of Boc-Phe-Gly-Leu-Gln-AMC, mp 234°–236° with decomposition. TLC with methanol:chloroform (1:9) showed a single spot, Rf 0.20.

Anal. Calcd. for $C_{37}H_{48}N_6O_9$: C, 61.64; H, 6.72; N, 11.66. Found: C, 61.44; H, 6.53; N, 11.56.

Boc-Phe-Gly-Leu-Gln-AMC (0.63 g) was deblocked by treatment with trifluoroacetic acid at about 23°. Toluene was added to the resulting reaction mixture, and then the combined solvents were evaporated at reduced pressure, leaving a residue. This residue was redissolved in toluene, and the solvent was then evaporated again to leave a residue, which was dried in vacuo overnight over solid potassium hydroxide to provide 0.69 g of white, solid H-Phe-Gly-Leu-Gln-AMC trifluoroacetate. TLC with 1-butanol:acetic acid: water (4:1:1) showed two spots, Rf 0.58 and Rf 0.51.

A solution of H-Phe-Gly-Leu-Gln-AMC trifluoroacetate (0.69 g, 0.94 mmol) was prepared in 4 mL 50% (V/V) water/dioxane and cooled to 0°. To this solution, solid sodium bicarbonate (0.16 g, 1.87 mmol) and a solution of succinic anhydride (0.11 g, 1.12 mmol) in 1 mL dioxane were added. The resulting reaction mixture was stirred for 1 hr at 0°. Additional sodium bicarbonate (0.16 g, 1.9 mmol) and succinic anhydride (0.11 mmol) were added to the reaction mixture, which was then warmed to about 23° and stirred for 1 hr. Hydrochloric acid (0.2N, 30 mL) was then added to the reaction mixture and the resulting mixture extracted with ethyl acetate. Insoluble material remaining in the combined aqueous and organic phases was separated by filtration, washed with 0.2N hydrochloric acid, and then dried to provide 0.36 g of crude Suc-Phe-Gly-Leu-Gln-AMC. The organic phase remaining from the ethyl acetate extraction was separated, washed with additional 0.2N hydrochloric acid, and dried over anhydrous sodium sulfate. Evaporation of solvent at reduced pressure left a residue (0.19 g) of crude Suc-Phe-Gly-Leu-Gln-AMC, which was combined with the other portion of crude product. The combined crude products (0.55 g total) were crystallized from methanol/ethyl acetate to provide 0.38 g purified Suc-Phe-Gly-Leu-Gln-AMC, mp 224°–225° with prior softening at 215°.

Anal. Calcd. for $C_{30}H_{33}N_5O_9$: C, 59.29; H, 5.48; N, 11.53. Found: C, 59.37; H, 6.17; N, 11.31.

EXAMPLE 2

Preparation of Suc-Phe-Gly-Leu-Gln-NA

Boc-Phe-Gly-Leu-Gln-NA was prepared by coupling Boc-Phe-Gly-Leu-OH (1.42 g, 3.25 mmol) to H-Gln-NA HCl (1.00 g, 3.25 mmol) by a mixed anhydride coupling procedure. A total of 10 mL DMF was used to dissolve H-Gln-NA HCl. During workup of the organic phase resulting from the mixed anhydride coupling procedure, some product crystallized and was separated, washed with water, and dried to yield 0.91 g of Boc-Phe-Gly-Leu-Gln-NA, mp 238°–239°. The remaining organic phase was washed with a saturated salt solution, and a second crop of crystalline product (0.62 g) was obtained, mp 238°–239°. A sample of the first crop was analyzed.

Anal. Calcd. for $C_{37}H_{48}N_6O_7$: C, 64.50; H, 7.04; N, 12.20. Found: C, 64.64; H, 6.96; N, 12.21.

Boc-Phe-Gly-Leu-Gln-NA (0.90 g) was deblocked by treatment with ethanolic HCl to yield 0.79 g of H-Phe-Gly-Leu-Gln-NA HCl. TLC in 1-butanol:acetic acid:water (4:1:1) indicated a major spot, Rf 0.61, and two trace spots, Rf 0.71 and Rf 0.51.

A solution of H-Phe-Gly-Leu-Gln-NA HCl (0.72 g, 1.15 mmol) was prepared in 4 mL DMF and cooled to 0°. Succinic anhydride (0.14 g, 1.38 mmol) and triethylamine (0.32 mL, 2.30 mmol) were added to this solution, and the resulting reaction mixture was stirred at 0° for 30 min, diluted with 0.2N hydrochloric acid, and extracted with ethyl acetate. The resulting ethyl acetate extract was washed with 0.2N hydrochloric acid, and then cooled to precipitate 0.52 g of Suc-Phe-Gly-Leu-Gln-NA, mp 230°–232°C. The remaining filtrate yielded a second crop of product crystals. (0.27 g) mp 230–232.5. Both crops of product crystals were combined and recrystallized from methanol to provide 0.53 g of purified Suc-Phe-Gly-Leu-Gln-NA, mp 238–239.5.

TLC with 1-butanol:acetic acid:water (4:1:1) indicated a major spot at Rf 0.74 and a minor spot at Rf 0.82.

Anal. Calcd. for $C_{36}H_{44}N_6O_8$: C, 62.76; H, 6.45; N, 12.20. Found: C, 62.71; H, 6.73; N, 12.01.

EXAMPLES 3–5

Assays of Virus-Specified Protease Activity Using Labelled Tetrapeptide Protease Substrates Examples 3–5, below, illustrate use of labelled tetrapeptide protease substrates of the present invention to assay viral protease activity in extracts of virus-infected cells. In Example 3, Suc-Phe-Gly-Leu-Gln-AMC was employed as substrate. In Example 4 and 5, both Suc-Phe-Gly-Leu-Gln-NA and Suc-Phe-Gly-Leu-Gln-AMC were employed. Examples 4 and 5 demonstrate that protease activity measured by NA-labelled and AMC-labelled substrates can be correlated.

EXAMPLE 3

A. Preparation of Cell Extracts 60 mm plates of HeLa-O cells were grown to confluence and infected with $6 \times 10^8$ pfu/plate of poliovirus type 2 (vaccine strain). After 1 hr, McCoy's growth media was added to each plate and the cells were incubated for an additional 4 hours. The cells were then removed from the plates, suspended in 10 mM tris(hydroxymethyl)aminomethane buffer, pH 7.3, containing 10 mM sodium chloride and 1.5 mM magnesium chloride. The resulting suspension was homogenized in a mechanical cell homogenizer and then centrifuged at $6,000 \times g$ for 10 minutes to remove insoluble cell debris. The supernatant was then recentrifuged at $30,000 \times g$ for 1 hour to provide a microsomal (pellet) and cytosol (supernatant) fractions, which were reserved for assay. Control fractions were prepared substantially similarly, except that uninfected HeLa-O cells were used.

B. Protease Assay

Total protein concentrations were determined by a dye-binding method employing Coomassie Brilliant Blue G-250 (Bio-Rad Protein Assay). Bovine serum albumin was used as a standard. Substrate Suc-Phe-Gly-Leu-Gln-AMC was stored as a $2 \times 10^{-2}$M stock solution in dimethylk sulfoxide. Assay solutions consisted of $2.0 \times 10^{-4}$M substrate in 50 mM sodium phosphate buffer, pH 5.0, containing 5 mM ethylenediaminetetraacetic acid (EDTA), 5 mM dithiothreitol (DTT), 0.10M sodium chloride, and 1% dimethyl sulfoxide. Each assay reaction was initiated by adding aliquots (0.01–0.10 mL) of cell extracts prepared as described above to 2.00 mL of assay solution. Viral protease activity, measured as liberation of free AMC, was determined by excitation at 380 nm and measurement of fluorescence emission at 460 nm. The fluorometer was standardized to provide a full scale deflection equivalent to $1.0 \times 10^{-7}$M AMC, and full scale was arbitrarily assigned as 100 units. The results of these assays are set forth in Table I, below. Results were normalized by reporting activity (units/min) per mg total protein to compensate for variations in preparation of cell extracts.

TABLE I

Protease Activity in Polio Virus P₂
Infected Cells Measured by Hydrolysis of
Suc-Phe-Gly-Leu-Gln-AMC (arbitrary units)

|  | Cytosol Fraction | Microsomal Fraction |
|---|---|---|
| Infected Cells | 41 | 38 |
| Control Cells | 16 | 22 |

EXAMPLE 4

Cell extracts of Poliovirus Type 2 infected HeLa-O cells and uninfected controls were prepared substantially as described in Example 3. Cells were grown in roller bottles, and test cultures were infected with $5 \times 10^{10}$ pfu of virus in 5 mL media, then incubated for 5 hours.

Protease activity in the resulting cell extracts was determined using Suc-Phe-Gly-Leu-Gln-AMC as substrate. The assay procedure was substantially similar to that described in Example 3, except the assay buffer employed contained 1 mM DTT in place of 5 mM DTT.

Protease activity in these extracts was also determined using Suc-Phe-Gly-Leu-Gln-NA as substrate. In these assays, each assay mix contained $2 \times 10^{-4}$ M substrate in 2 mL of an assay buffer containing 50 mM sodium phosphate, pH 6.0, 0.1M sodium chloride, 5 mM EDTA, 1 mM DTT, and 2.5% dimethyl sulfoxide. Substrate was added to assay mixtures from a stock solution of $2 \times 10^{-2}$ M substrate in dimethyl sulfoxide. Activity was determined by excitation at 335 nm and measurement of emission at 410 nm.

The results of these protease assays are set forth in Table II, below.

TABLE II

Protease Activity in Cytosol Fractions of
Poliovirus P₂-Infected Cells Measured by
Hydrolysis of Suc-Phe-Gly-Leu-Gln-AMC and
Suc-Phe-Gly-Leu-Gln-NA

| Sample | Protease Activity: Units/min/mg Protein | |
|---|---|---|
|  | AMC Substrate | NA Substrate |
| Infected Cells | 22.5 | 3.24 |
| Control Cells | 11.4 | 1.86 |

EXAMPLE 5

60 mm plates containing HeLa-O cells were grown to confluence and then infected with $1.2 \times 10^8$ pfu of Poliovirus Type 2. After 1 hour of incubation, McCoy's growth media was added to each plate and the cells were incubated for an additional two hours or four hours. After harvesting, cells were suspended in 10 mM tris(hydroxymethyl)aminomethane buffer, pH 7.3, containing 10 mM sodium chloride and 1.5 mM magnesium chloride, homogenized, and centrifuged at $6{,}000 \times g$ for 10 minutes. Control cells were treated substantially similarly except for addition of virus.

The resulting cell extracts were assayed for protease activity using Suc-Phe-Gly-Leu-Gln-AMC as substrate, substantially as described in Example 3, above.

In addition, the extracts were assayed as follows by a colorimetric procedure employing Suc-Phe-Gly-Leu-Gln-NA. A stock solution of Suc-Phe-Gly-Leu-Gln-NA at $2 \times 10^{-2}$ M in dimethyl sulfoxide was prepared, and used to prepare an assay solution containing 40 μL substrate stock solution, 60 μL dimethyl sulfoxide, and 4 mL 50 mM sodium phosphate buffer, pH 5.0, containing 5 mM EDTA, 1 mM DTT, and 0.10M sodium chloride. 50 μL of cell extract aliquots of cell extracts were incubated with 50 μL of assay solution, and color was developed using the reagents and procedure described by Barrett, *Anal. Biochem.* 76:374-376 (1976). The resulting samples were scored visually for red color.

The results of these assays are set forth in Table III, below.

TABLE III

Protease Activity in Crude Extracts
of Cells Infected with Poliovirus P2 Measured
by Hydrolysis of Suc-Phe-Gly-Leu-Gln-AMC and
Suc-Phe-Gly-Leu-Gln-NA

|  | Protein (mg/mL) | Protease Activity | |
|---|---|---|---|
|  |  | AMC Substrate (Units/min/mg) | NA Substrate (relative color) |
| Infected Cells (2 hours) | 8.25 | 12.1 | ++ |
| Infected Cells (4 hours) | 7.97 | 22.2 | +++ |
| Control Cells (4 hours) | 6.97 | 10.5 | + |

What is claimed is:

1. A compound of the formula $$R^1\text{-}[A^4A^3A^2A^1]\text{-}R^2,$$

or a physiologically acceptable salt thereof, wherein
   $A^1$ is an amino acid residue Asn;
   $A^2$ is an amino acid residue selected from the group consisting of Ala, Leu, Ile, and Val;
   $A^3$ and $A^4$ are, independently, amino acid residues of D- or L-configuration selected from the group consisting of Ala, Arg, Asn, Asp, Cys, Gln, Glu, gly, His, Ile, Leu, Lys, Met, Phe, Pro, Ser, Thr, Trp, Tyr, Val, and analogues thereof;
   $R^1$ is hydrogen or an N-terminal protecting group; and
   $R^2$ is X and X is a chromogenic, fluorogenic, chemiluminescent, radioactive, antigenic, or haptenic indicator group.

2. A compound according to claim 1, wherein $R^1$ is selected from the group consisting of Z, Boc, Suc, and MeOSuc.

3. A compound according to claim 2, wherein $A^3$ and $A^4$ are independently selected from the group consisting of Ala, Arg, Asp, Cys, Gln, Glu, Gly, His, Ile, Leu, Lys, Met, Phe, Pro, Ser, Thr, Tyr, Val, Trp, and Asn.

4. A compound according to claim 3, wherein $A^3$ and $A^4$ are independently selected from the group consisting of Ala, Gly, Ile, Leu, Phe, Ser, Tyr and Val.

5. A method for detecting picornavirus activity in a sample, comprising
   (a) forming an assay mixture by contacting a quantity of the sample with a compound of the formula $$R_1\text{-}[A^4A^3A^2A^1]\text{-}R^2.$$

or a physiologically acceptable salt thereof, wherein
   $A^2$ is an amino acid residue Asn;
   $A^2$ is an amino acid residue selected from the group consisting of Ala, Leu, Ile, and Val;
   $A^3$ and $A^4$ are, independently, amino acid residues of D- or L-configuration selected from the group consisting of Ala, Arg, Asn, Asp, Cys, Gln, Glu, Gly His, Ile, Leu, Lys, Met, Phe, Pro, Ser, Thr, Trp, Tyr, Val, and analogues thereof;

$R^1$ is hydrogen of an N-terminal protecting group; and $R^2$ is —X, where X is a chromogenic, fluorogenic, chemiluminescent, radioactive, antigenic, or haptenic indicator group;

(b) incubating the assay mixture for a time sufficient to permit hydrolysis of the indicator group if protease activity is present; and (c) detecting the presence of free indicator group in the assay mixture.

* * * * *